(12) United States Patent
Buerger et al.

(10) Patent No.: US 10,762,647 B2
(45) Date of Patent: Sep. 1, 2020

(54) MOTION COMPENSATION IN HYBRID X-RAY/CAMERA INTERVENTIONS

(71) Applicant: KONINKLIJKE PHILIPS N.V., Eindhoven (NL)

(72) Inventors: Christian Buerger, Hamburg (DE); Michael Grass, Buchholz in der Nordheide (DE); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 16/099,484

(22) PCT Filed: May 19, 2017

(86) PCT No.: PCT/EP2017/062054
§ 371 (c)(1),
(2) Date: Nov. 7, 2018

(87) PCT Pub. No.: WO2017/198799
PCT Pub. Date: Nov. 23, 2017

(65) Prior Publication Data
US 2019/0206069 A1    Jul. 4, 2019

(30) Foreign Application Priority Data

May 19, 2016    (EP) ..................... 16170451

(51) Int. Cl.
*A61B 6/00*    (2006.01)
*G06T 7/32*    (2017.01)
(Continued)

(52) U.S. Cl.
CPC ............... *G06T 7/32* (2017.01); *A61B 34/20* (2016.02); *A61B 90/37* (2016.02); *G06T 3/0068* (2013.01);
(Continued)

(58) Field of Classification Search
CPC .............................. A61B 90/37; G06T 7/00
(Continued)

(56) References Cited

U.S. PATENT DOCUMENTS 8,398,541 B2    3/2013    Dimaio
2005/0281385 A1    12/2005    Johnson
(Continued)

FOREIGN PATENT DOCUMENTS

WO    199927839 A2    6/1999
WO    2012095755 A1    7/2012
WO    2016044934 A1    3/2016

*Primary Examiner* — Abolfazl Tabatabai

(57) ABSTRACT

A system and method of assisting a treatment procedure is provided, the method comprising the steps of determining a 3-D intervention vector in relation to an inner body structure of a body of interest based on a 3-D x-ray image, determining a 3-D position of an entry point on an outer surface of the body of interest based on the intervention vector, comparing the position and/or orientation of the inner body structure in the 3-D x-ray image with the position and/or orientation of the inner body structure in an additional 2-D x-ray image being generated transverse to the intervention vector, correcting the 3-D position of the entry point on the outer surface of the body of interest based on a deviation detected in the comparing step.

15 Claims, 4 Drawing Sheets

(51) Int. Cl.
  *G06T 7/33*    (2017.01)
  *A61B 34/20*   (2016.01)
  *A61B 90/00*   (2016.01)
  *G06T 3/00*    (2006.01)
  *G06T 7/00*    (2017.01)

(52) U.S. Cl.
  CPC ............... *G06T 7/33* (2017.01); *G06T 7/337* (2017.01); *A61B 2034/2051* (2016.02); *A61B 2034/2057* (2016.02); *A61B 2034/2065* (2016.02); *A61B 2034/2072* (2016.02); *A61B 2090/367* (2016.02); *A61B 2090/376* (2016.02); *G06T 2207/10024* (2013.01); *G06T 2207/10116* (2013.01); *G06T 2207/30004* (2013.01)

(58) Field of Classification Search
  USPC ......................................................... 382/133
  See application file for complete search history.

(56) References Cited

U.S. PATENT DOCUMENTS

| | | |
|---|---|---|
| 2006/0115054 A1 | 6/2006 | Yatsenko |
| 2008/0119728 A1 | 5/2008 | Frenkel |
| 2009/0036902 A1* | 2/2009 | DiMaio ................ A61B 34/37 606/130 |
| 2011/0268333 A1 | 11/2011 | Klingenbeck |

* cited by examiner

MOTION COMPENSATION IN HYBRID X-RAY/CAMERA INTERVENTIONS

CROSS-REFERENCE TO PRIOR APPLICATIONS

This application is the U.S. National Phase application under 35 U.S.C. § 371 of International Application No. PCT/EP2017/062054, filed on May 19, 2017, which claims the benefit of European Patent Application No. 16170451.5, filed on May 19, 2016. These applications are hereby incorporated by reference herein.

FIELD OF THE INVENTION

The invention relates to the field of computer based assistance of surgery. In particular, the invention relates to a system and method of automatic image processing including an interpretation of the content of for example an x-ray image. The method may be implemented as a computer program executable on a processing unit of a suitable device.

BACKGROUND OF THE INVENTION

In every surgery where intraoperative imaging is used it is a challenge to accurately perform the necessary steps of a procedure of treating a bone. Usually, almost each step requires an iterative process based on several X-ray images. A significant radiation exposure is thus produced. The amount of radiation may be highly dependent on the know-how and skill of the physician.

US 2008/0119728 A1 describes a system for video based registration between images during a skeletal medical procedure, the system includes a stereoscopic camera, a two dimensional image detector and a registration processor, the stereoscopic camera is associated with a stereoscopic coordinate system, the stereoscopic camera acquires a stereoscopic image pair of a fiducial mark, the fiducial mark is fixed onto a skeletal structure, a first fiducial representation of the fiducial mark is apparent on the stereoscopic image pair, the 2D image detector is associated with a 2D coordinate system and acquires at least two substantially different images of the skeletal structure, a second fiducial representation of the fiducial mark and a first skeletal representation of the skeletal structure is apparent on the two substantially different 2D images, the registration processor is coupled with the stereoscopic camera and with the 2D image detector and registers the stereoscopic coordinate system with a three dimensional (3D) coordinate system associated with a volumetric image detector, and superimposes 3D information on at least one volumetric image acquired by the volumetric image detector, according to the registration, the registration processor registers the stereoscopic coordinate system with the 3D coordinate system by registering the stereoscopic coordinate system with the 2D coordinate system using the first fiducial representation apparent in the stereoscopic image pair, and the second fiducial representation apparent in the two substantially different 2D images, and by registering the 2D coordinate system with the 3D coordinate system using the first skeletal representation apparent in the two substantially different 2D images, and the second skeletal representation apparent in the at least one volumetric image.

SUMMARY OF THE INVENTION

It may be seen as an object of the invention to provide a device for more efficiently assisting in performing a surgical procedure. It would be of high benefit to reduce the amount of radiation to which a patient is exposed, and to have a more efficient way to directly evaluate the content of images or to move to a next step of a workflow.

The mentioned objects are solved by the subject-matter of each of the independent claims. Further embodiments are described in the respective dependent claims.

In general, a device for assisting a treatment procedure may comprise an x-ray device with an x-ray source and an x-ray detector, wherein the x-ray device is configured to generate 2-D projection images of a body of interest from different angles relative to the body of interest, a camera, wherein the camera is configured to generate an image with an imaging direction of an outer surface of the body of interest, and wherein the camera is arranged in a predetermined relation to the x-ray device, and a processing unit for processing the image data from the x-ray device and the image data from the camera.

The processing unit may be configured to reconstruct a 3-D image of a body of interest based on a plurality of 2-D projection images generated from different angles relative to the body of interest, to determine a direction of an intervention to be performed on an inner body structure, to receive a single 2-D projection image with a projection direction being transverse to the direction of the intervention, to register the single 2-D projection image with the 3-D image, to detect a deviation of a position and/or orientation of an inner body structure as visualized in the virtual projection image from the position and/or orientation of the inner body structure as visualized in the single 2-D projection image, and to indicate in the camera image a position on the outer surface for the intervention to be performed on the inner body structure.

It is noted, that the processing unit may be realized by only one processor performing all the steps of the method, or by a group or plurality of processors, for example a system processor for processing the image data, a separate processor specialized on a determination of geometrical aspects, and a further processor for controlling a monitor for visualizing results.

The step of registering the single 2-D projection image with the 3-D image may include an identification of a specific projection image out of the plurality of 2-D projection images, the specific projection images being acquired under the same projection direction as the projection direction of the single 2-D projection image. Further, the scales and the orientation of image content may be adapted in similar 2-D images relative to each other, so as to register one image with another one.

According to another embodiment, the device may further comprise an input unit for receiving an input for interactively controlling the computer program element and thus a workflow of the device. The input unit may be for example a computer keyboard, a computer mouse or a touch screen, so that the input unit may be adapted for manually identifying geometrical aspects of an inner body structure like a bone in an image. Otherwise, the input unit may further include an electronic interface for receiving data sets representing a workflow of a procedure. By means of such an input device, a frame may be draw enclosing one or more vertebral bodies, for example.

According to an embodiment, the processing unit may further be configured to automatically identify a region of interest in the 3-D image and to identify a corresponding region of interest in the single 2-D projection image, and wherein the registering of the single 2-D projection image with the 3-D image is limited to the region of interest, the region of interest including the inner body structure. It will be understood that the identification of an inner body structures and/or of a region of interest may also be performed for example as a combination of a manual indication of an inner body structure and a subsequent automatic definition of a region of interest enclosing that inner body structure.

As used herein, the term "inner body structure" refers for example to anything at a bone and in particular to a geometrical aspect of a bone, i.e. a point, a line, an arc, a center point, an axis, a cylinder surface, a ball surface, or the like. An inner body structure may in particular be a structure which is manually or automatically distinguishable on the basis of an x-ray image from surrounding structures. For example, a vertebral body of a spine can be identified as the surrounding soft tissue has a different appearance in an x-ray image.

According to another embodiment, the processing unit may further be configured to detect a deviation of positions and/or orientations of not only one but of a plurality of inner body structures. The processing unit may then be configured to take into account interrelations between the plurality of inner body structures when determining the position on the outer surface to be indicated in the camera image.

According to further embodiment, the imaging direction of the camera may be alignable to the direction of the intervention. This may for example be possible, when the x-ray device is a c-arm based x-ray device and the camera is fixedly attached to a housing of the x-ray detector.

According to yet another embodiment, the processing unit may further be configured to identify in the 3-D image a position of at least one landmark on the outer surface of the body of interest, to identify in the camera image a position of the at least one landmark on the outer surface of the body of interest, wherein the position for an intervention is indicated in the camera image in relation to the position of the at least one landmark.

The device may thus further comprise an element configured to be attached to the outer surface of the body of interest, wherein the at least one landmark is formed by the element. Such a landmark may in particular be useful when an interrelation between the x-ray device and the camera is not predetermined, for example when the camera is not fixedly attached to the x-ray device.

Finally, the device may further comprise a monitor for visualizing information.

According to another aspect, a computer program element may be provided which is executable on the processing unit of the above described device. The computer program element may generally comprise sets of instructions for receiving a plurality of 2-D projection images generated from different angle relative a body of interest, generating a 3-D image of the body of interest based on the plurality of 2-D projection images, receiving a further projection image with a projection direction being transverse to a direction of an intended intervention, registering the further projection image with a specific projection image out of the plurality of 2-D projection images, the specific projection images being acquired under the same projection direction as the projection direction of the further projection image, determining a deviation of an inner body structure in the specific projection image from the inner body structure in the further projection image, receiving a camera image of an outer surface of the body of interest, and indicating in the camera image a position of an entry point on the outer surface for the intended intervention on the inner body structure.

That is, at least the mentioned aspects of the procedure can be performed automatically. It is noted that these aspects do not include any step of an intervention on a patient. In other words, the automatically performed steps of the procedure do not include any steps of treatment of a human body by surgery.

By means of the computer program element, contour lines or points of an inner body structure may be automatically detected and/or identified in an x-ray image, for example based on grayscale values of pixels which can be identified and compared with adjacent grayscale values.

In other words, the determined deviation may be translated by the processing unit into a necessary adjustment of an interventional device, for example a handling device being outside of a body of a patient. The kind and degree of the adjustment may be optically or acoustically provided.

The computer program element may further comprise sets of instructions for defining a region of interest including the inner body structure, both in the specific projection image and in the further projection image, wherein the registering is limited to the region of interest.

In accordance with an embodiment, the computer program element may further comprise sets of instructions for determining in the 3-D image a direction of the intended intervention of the inner body structure.

According to further embodiment, the computer program element may further comprise sets of instructions for controlling the imaging direction of the camera so as to align the same to the direction of the intended intervention. For example, when the camera is fixedly connected to the c-arm of the x-ray device, the computer program element may control the movement of the c-arm to achieve the alignment of the camera.

The computer program element may preferably be loaded into a work memory of a data processor. The data processor or processing unit is thus equipped to carry out the method. Further, the invention relates to a computer-readable medium such as a CD-ROM at which the computer program element may be stored. However, the computer program element may also be presented over a network like the World Wide Web and can be downloaded into the working memory of the data processor from such a network.

According to another aspect, a method of assisting a treatment procedure is provided, the method comprising the steps of determining a 3-D intervention vector in relation to an inner body structure of a body of interest based on a 3-D x-ray image, determining a 3-D position of an entry point on an outer surface of the body of interest based on the intervention vector, comparing the position and/or orientation of the inner body structure in the 3-D x-ray image with the position and/or orientation of the inner body structure in an additional 2-D x-ray image being generated transverse to the intervention vector, correcting the 3-D position of the entry point on the outer surface of the body of interest based on a deviation detected in the comparing step.

In accordance with an embodiment, the method does not include any step of treatment of the patient's body by surgery. In other words, the invention concerns aspects beside the interventional steps.

According to an embodiment, the method may further comprise the step of determining at least one 3-D intervention vector in relation to a plurality of inner body structures of a body of interest based on a 3-D x-ray image. The step of comparing may encompass positions and/or orientations of the plurality of inner body structures. In particular, in the example of a spine, it will be understood that a movement of one vertebral body due to an interventional action may cause a movement of an adjacent neighbouring body.

The step of comparing the position and/or orientation of at least one of the inner body structure may further include an identification of a landmark in both the 3-D x-ray image and the additional 2-D x-ray image. As long as a relation of the x-ray imaging parameter and the camera imaging parameter is not predetermined, the landmark may provide a link between an x-ray image and a camera image.

According to an embodiment, the method further comprises the step of providing in a camera image an indication of the entry point on the outer surface of the body of interest. Such an indication may be a virtual point inserted into that image or may be for example a point actually generated by a laser pointer on the outer surface of the patient's body.

According to yet another embodiment, the method may further comprise the step of aligning an imaging direction of the camera with a 3-D intervention vector. When looking in a specific direction with the camera, a physician may receive information regarding a direction of the intended intervention. In combination with the previously described aspect, a physician may receive hints from the device which show the entry point and indicate a direction of intervention.

It has to be noted that embodiments are described with reference to different subject-matters. In particular, some embodiments are described with reference to method type claims (computer program) whereas other embodiments are described with reference to apparatus type claims (system). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Figure 1A:
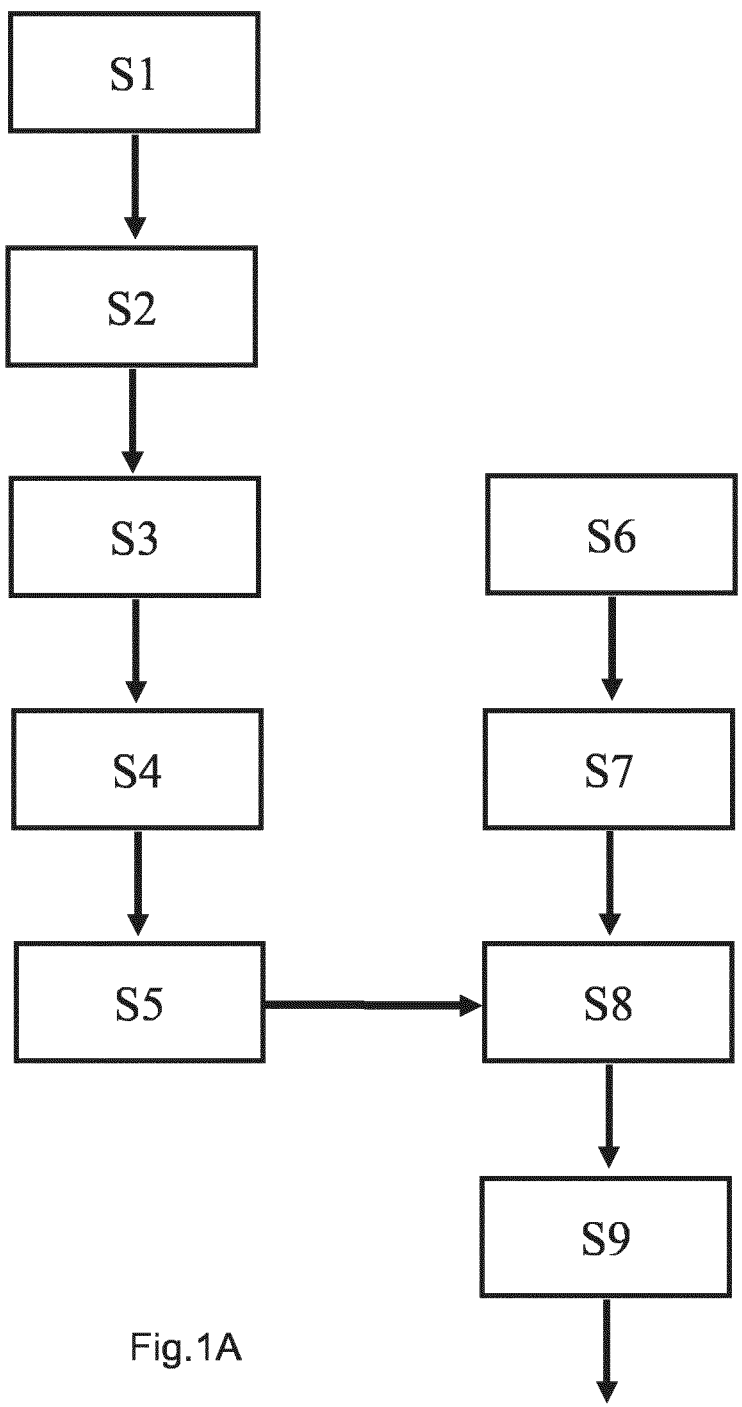
FIGS. 1a and 1b show a flow chart of steps of a method.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EMBODIMENTS

Figure 1B:
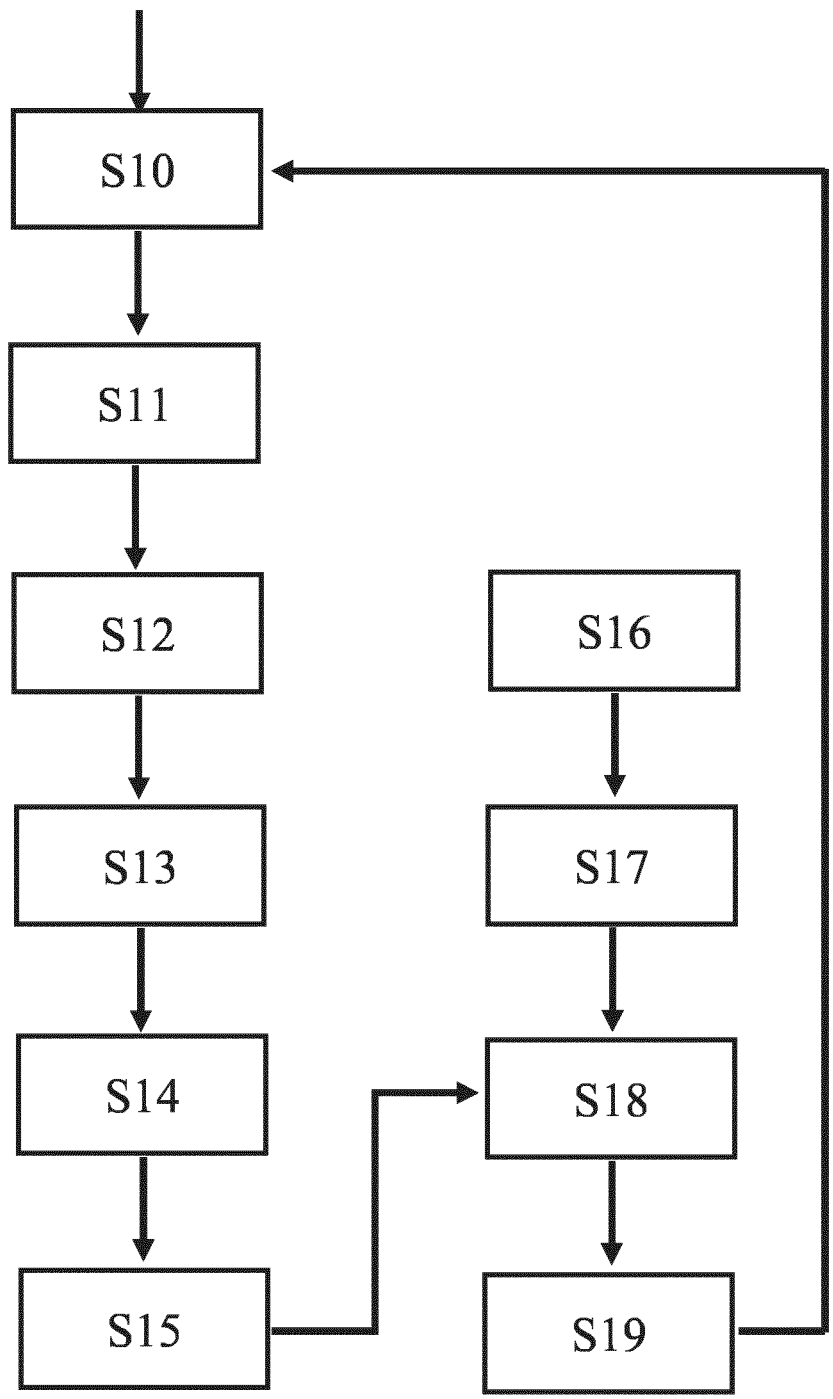

The flow-chart in FIGS. 1a and 1b (first page FIG. 1a and second page FIG. 1b) illustrates steps performed in accordance with embodiments. It will be understood that the steps described, may be major steps, wherein these major steps might be differentiated or divided into several sub-steps. Furthermore, there might be also sub-steps between the steps.

In the following, a method is described illustrating assistance in form of information for a surgeon performing, as an example, an implantation of a fixation structure at vertebral bodies of a human spine. The principles described in this example may also be applied so as to assist a surgeon when fixing a fracture at a bone of a human body.

It is noted that some steps are described as being performed "if necessary". This is intended to indicate that those steps may be omitted.

The method starts at an instance in which a patient is laying on an operation table and is prepared for an intervention at the spine.

In step S1 of the method, a plurality of 2-D projection images is generated from different imaging directions. For example, a C-arm based x-ray imaging system may move around the patient on the operation table and generate in a fast sequence the plurality of projection images. In step S2, a 3-D image is generated or reconstructed on the basis of such 2-D projection images.

In step S3, a landmark may be identified in the 3-D image. The landmark may be a separate element which may be fixed on the outer surface of the patient prior to the start of the procedure or during the procedure. The landmark may in particular be used as a kind of an anchor point allowing an identification of a position in a camera image. By means of such a landmark, it is possible to indicate a position at an outer surface of the patient's body in an image, which position may correlate to a position of an inner body structure which is only visible in the x-ray image.

In step S4, an inner body structure of interest is identified in the 3-D image. For example, a vertebral body may be such an inner body structure. A relation of the position and/or the orientation of the inner body structure may be determined relative to the landmark, at least when a landmark is used.

Furthermore, a position of an intended intervention on an outer surface is identified in the 3-D image in step S5. Also here, a relation to a landmark may be determined.

In step S6, a camera image is generated. The camera image may show an outer surface of the patient generally in the region of the intervention, i.e. above the inner body structure of interest.

If a landmark is used, the landmark is identified in the camera image in step S7. In step S8, a position for the intended intervention is shown in the camera image. This means, that a virtual sign may be inserted into the camera image showing or indicating a position on the outer surface of the patient through which an interventional instrument or implant may be inserted into the patient, with the instrument or implant aiming at the intended structure inside the body. Alternatively, the camera image may show a light point like a laser point on the surface of the body, wherein such a light point may be emitted onto the outer surface or skin by means of an appropriate light source. Consequently, a physician will get an indication as to where he has to insert implant so as to position the implant within an inner body structure without actually seeing that inner structure.

It is noted that the landmark may be used to correlate the position of the intended intervention on the outer surface in the camera image with the position of the intended intervention as determined based on the 3-D x-ray image. Otherwise, that correlation may also be achieved without a physical landmark or landmark element. For example, the imaging direction of the camera may be known in relation to the imaging direction of the x-ray device, i.e. based on two known coordinate systems it is possible to translate the point of interest from the x-ray system to the camera image. Furthermore, it may be possible to generate an image of an outer surface based on the 3D-image data, with a viewing direction which corresponds to the imaging direction of the camera, even if the camera is not attached to the x-ray device. It may be sufficient to know the relation of the camera relative to the body of the patient.

In step S9, the physician may perform an interventional step, i.e. will act with forces on body structures of the patient. By way of forcing the structures of the patient, the physician might shift or move such structures. For example, the physician may insert a nail or screw into one of the vertebral bodies and may cause adjacent vertebral bodies to change their current position and/or orientation.

In step S10, a single 2-D projection image is generated. That projection image is a side view onto the inner body structures of interest, i.e. has a projection direction which allows an identification of the body structures of interest and in particular a determination of a movement of such body structures within a plane, which plane includes the intervention direction or the direction of the applied force.

In step S11, a region of interest is determined which region includes the inner body structure. For example, a frame may be drawn enclosing the inner body of interest. The region of interest may be determined both in the single 2-D projection image and in the 3-D image, or at least in a 2-D image out of the plurality of images which form the basis for the 3-D image, wherein the 2-D image has a projection direction which corresponds to the projection direction of the additional single 2-D projection image.

The region of interest may have a size which is only a part of the 2-D image. In particular, the region of interest may be only slightly larger than the inner body structure of interest. For example, the region of interest may be a frame having a dimension which may be up to 20% larger than a diameter of the inner body structure. Otherwise, the region of interest may have a contour which follows the contour of the body structure of interest.

In step S12, the single 2-D projection image is registered with the 3-D image or at least with the corresponding 2-D projection image out of the plurality of images forming the basis for the 3-D image. In case, a smaller portion of the images is determined as a region of interest, only the region of interest in the single 2-D projection image is registered with the region of interest in the 3-D image.

In step S13, any changes of the position and/or orientation of the inner body structure of interest may be determined based on the registered images. The accuracy of the determination of any changes or of any deviation may be improved when the images are registered only within a previously determined region of interest.

Based on the determined deviation, a new vector for a following interventional action can be calculated in step S14. The new vector takes into account the current position and orientation of the inner body structure of interest, wherein that body structure of interest may also be a body structure adjacent to the already treated body structure. The intersection of the vector and the outer surface will be the insertion point for the intended next interventional step. The determination of that insertion point is performed in step S15. It is again noted that all these interventional steps are not part of the intervention.

In step S16, a further camera image is generated. As described above, a landmark may be identified in that camera image (step S17), and the position as determined in step S15 is visualized in the camera image in step S18 (virtually or also visible on the outer surface of the patient).

The intervention may continue with a next interventional action in step S19. As indicated by an arrow extending from S19 to S10 in FIG. 1B, steps S10 to S19 may be repeated.

Figure 2:
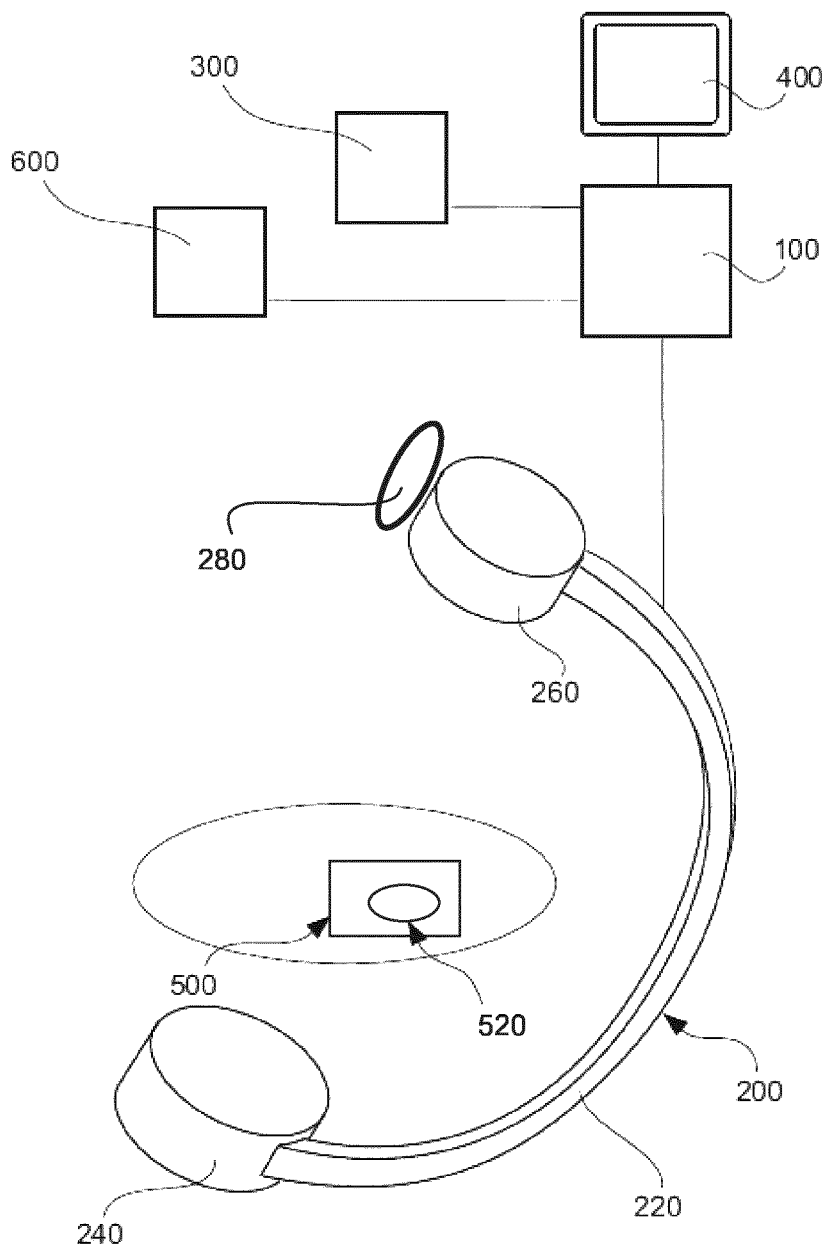
FIG. 2 shows a schematical illustration of a system.

FIG. 2 shows an exemplary embodiment of a device. Substantially, necessary for performing the steps of the method, a processing unit 100 is part of the device.

An exemplary imaging device 200 includes an X-ray source 240, and an X-ray detector 260, wherein these two units are mounted on a C-arm 220. At the housing of the X-ray detector, a camera 280 is fixedly attached. Thus, a relation between the viewing direction of the camera and the imaging direction of the x-ray device may be known.

Furthermore, the system in FIG. 2 includes an input unit 300, by means of which for example an intended imaging direction may be manually entered. Also shown is a connection to a database 600, located for example in a network. The database 600 may comprise information regarding anatomical structures, for example from 3D scans of different anatomical structures, so that the imaged anatomical structure may be compared with this information so as to automatically determine specific anatomical structures. The database may further comprise information regarding a sequence of necessary and/or possible steps of a surgical procedure. It is noted that it is also possible to automatically determine the progress of the surgical procedure based on detectable aspects in an x-ray image, wherein such aspects may be an instrument and/or implant.

Finally, there is an indication in FIG. 2 of a region of interest 500 as well as of a body structure 520 located within that region of interest. The body structure of interest may for example be a bone of a patient.

Figure 3:
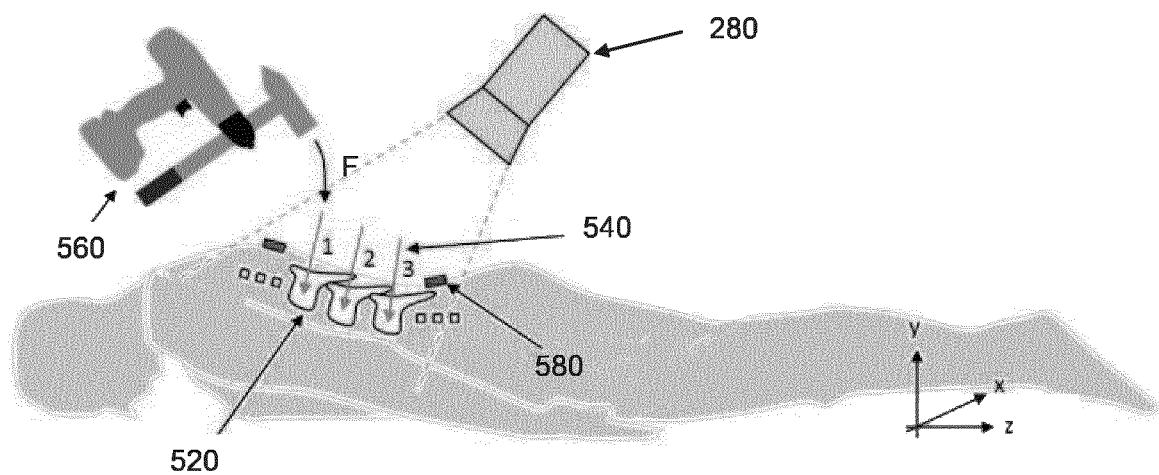
FIG. 3 is an example in which a spine of a patient is treated assisted by a disclosed device.

As an example, FIG. 3 illustrates a hybrid minimally invasive surgery for inserting three pedicle screws for spinal fusion purposes. In such hybrid surgery, optical markers or landmarks 580 may be attached onto the patient so that a camera 280 can recognize the patient's body surface. The internal anatomy may be derived from a 3D-CT scan. Model-based image segmentation can be applied to delineate body structures of interest (vertebrae 520) and to compute the insertion plan (arrows 540). With a known correlation of the coordinate systems of the camera 280 and the CT x-ray device, internal body structures 520 as well as the insertion plan in form of interventional vectors 540 can be overlaid onto the patient's skin surface and presented to the surgeon for example on a display like that shown in FIG. 4.

Instead of acquiring a full 3D scan for controlling the current position and orientation of the body structures of interest, it is proposed to acquire a single 2D projection (minimal dose required) to achieve information related to a deformation between internal body structures and the patient's skin surface. In case of the minimally invasive surgery in FIG. 3, application of a force F by means of a tool 560 like a hammer or a drill on the first implant (not shown) will most likely leads to a deformation substantially along the insertion path and thus within the yz-plane. Once the first implant is being inserted, a single 2D X-ray projection within yz may be acquired. This plane is registered onto the corresponding yz projection of the originally acquired CT scan to realign the anatomy with the patient's body surface. This registration is guided by the segmentation model which was applied to delineate each vertebra. Non-rigid tissue deformation is approximated by applying multiple rigid/affine registrations, one for each vertebra. With this corrected/updated insertion plan, a second screw (also not shown) may be inserted with a higher accuracy. The same procedure using 2D image acquisition and model-guided image registration may be repeated for insertion of the third screw (not shown).

Figure 4:
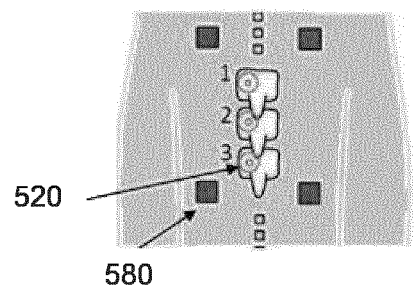
FIG. 4 is an example of a camera image.

It is noted that the imaging direction of the camera 280 in FIG. 3 is slight inclined relative to the direction of the intended intervention vectors 540 whereas the imaging direction of the camera in FIG. 4 is aligned with the direction of the intended intervention, i.e. the vector of the interventional direction is shown as a point.

While embodiments have been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS 100 processing unit
200 imaging device
220 C-arm
240 X-ray source
260 X-ray detector
280 camera
300 input device
400 monitor
500 region of interest
520 inner body structure
540 vector of intervention
560 tool
580 landmark
600 database

The invention claimed is:

1. A device for assisting a treatment procedure, comprising:
an x-ray device with an x-ray source and an x-ray detector, wherein the x-ray device is configured to generate 2-D projection images of a body of interest from different angles relative to the body of interest,
a camera, wherein the camera is configured to generate an image with an imaging direction of an outer surface of the body of interest, and wherein the camera is arranged in a predetermined relation to the x-ray device,
a processing unit for processing the image data from the x-ray device and the image data from the camera, wherein the processing unit is configured
to reconstruct a 3-D image of the body of interest based on a plurality of 2-D projection images generated from different angles relative to the body of interest,
to determine a direction of an intervention to be performed on an inner body structure,
to receive a single 2-D projection image with a projection direction being transverse to the direction of the intervention,
to register the single 2-D projection image with the 3-D image,
to detect a deviation of a position and/or orientation of an inner body structure as visualized in the virtual projection image from the position and/or orientation of the inner body structure as visualized in the single 2-D projection image, and
to indicate in the camera image a position on the outer surface for the intervention to be performed on the inner body structure.

2. The device of claim 1, wherein the processing unit is further configured to identify a region of interest in the 3-D image and to identify a corresponding region of interest in the single 2-D projection image, and wherein the registering of the single 2-D projection image with the 3-D image is limited to the region of interest, the region of interest including the inner body structure.

3. The device of claim 1, wherein the processing unit is further configured to detect a deviation of positions and/or orientations of a plurality of inner body structures, and wherein the processing unit is further configured to take into account interrelations between the plurality of inner body structures when determining the position on the outer surface to be indicated in the camera image.

4. The device of claim 1, wherein the imaging direction of the camera is alignable to the direction of the intervention.

5. The device of claim 1, wherein the x-ray device is a c-arm based x-ray device and wherein the camera is fixedly attached to the x-ray device.

6. The device of claim 1, wherein the processing unit is further configured
to identify in the 3-D image a position of at least one landmark on the outer surface of the body of interest,
to identify in the camera image a position of the at least one landmark on the outer surface of the body of interest,
wherein the position for an intervention is indicated in the camera image in relation to the position of the at least one landmark.

7. The device of claim 6, further comprising an element configured to be attached to the outer surface of the body of interest, wherein the at least one landmark is formed by the element.

8. A computer program element executable on the processing unit of the device according to claim 1, the computer program element comprising sets of instructions for:
receiving a plurality of 2-D projection images generated from different angle relative a body of interest,
generating a 3-D image of the body of interest based on the plurality of 2-D projection images,
receiving a further projection image with a projection direction being transverse to a direction of an intended intervention,
registering the further projection image with a specific projection image out of the plurality of 2-D projection images, the specific projection images being acquired under the same projection direction as the projection direction of the further projection image,
determining a deviation of an inner body structure in the specific projection image from the inner body structure in the further projection image, receiving a camera image of an outer surface of the body of interest, and indicating in the camera image a position of an entry point on the outer surface for the intended intervention on the inner body structure.

9. The computer program element of claim 8, further comprising sets of instructions for defining a region of interest including the inner body structure, both in the specific projection image and in the further projection image, wherein the registering is limited to the region of interest.

10. The computer program element of claim 8, further comprising sets of instructions for determining in the 3-D image a direction of the intervention of the inner body structure.

11. A method of assisting a treatment procedure, the method comprising the steps of determining a 3-D intervention vector in relation to an inner body structure of a body of interest based on a 3-D x-ray image, determining a 3-D position of an entry point on an outer surface of the body of interest based on the intervention vector, comparing the position and/or orientation of the inner body structure in the 3-D x-ray image with the position and/or orientation of the inner body structure in an additional 2-D x-ray image being generated transverse to the intervention vector, correcting the 3-D position of the entry point on the outer surface of the body of interest based on a deviation detected in the comparing step.

12. The method of claim 11, wherein the method comprises the step of determining a 3-D intervention vector in relation to a plurality of inner body structures of a body of interest based on a 3-D x-ray image, and wherein the step of comparing encompasses positions and/or orientations of the plurality of inner body structures.

13. The method of claim 11, wherein the step of comparing the position and/or orientation of at least one of the inner body structure includes an identification of a landmark in both the 3-D x-ray image and the additional 2-D x-ray image.

14. The method of claim 11, further comprising the step of providing in a camera image an indication of the entry point on the outer surface of the body of interest.

15. The method of claim 11, further comprising the step of aligning an imaging direction of the camera with the 3-D intervention vector.

* * * * *